(12) United States Patent
Cai et al.

(10) Patent No.: US 8,353,954 B2
(45) Date of Patent: Jan. 15, 2013

(54) PROSTHETIC HEART VALVE INCLUDING STENT STRUCTURE AND TISSUE LEAFLETS, AND RELATED METHODS

(75) Inventors: Chad Cai, Woodbury, MN (US); Peter Nicholas Braido, Maple Grove, MN (US); Bob Allan, Maple Grove, MN (US); Paul Edward Ashworth, Wyoming, MN (US); Steve Kruse, St. Michael, MN (US); Lise LaChance, Santa Rosa, CA (US)

(73) Assignee: St. Jude Medical, Inc., St. Paul, MN (US)

( * ) Notice: Subject to any disclaimer, the term of this patent is extended or adjusted under 35 U.S.C. 154(b) by 0 days.

(21) Appl. No.: 12/004,170

(22) Filed: Dec. 19, 2007
(Under 37 CFR 1.47)

(65) Prior Publication Data

US 2008/0147179 A1 Jun. 19, 2008

Related U.S. Application Data

(60) Provisional application No. 60/875,921, filed on Dec. 19, 2006.

(51) Int. Cl.
*A61F 2/24* (2006.01)
(52) U.S. Cl. .......................... 623/2.14; 623/2.4; 623/915
(58) Field of Classification Search ................. 623/2.13, 623/2.38, 2.4, 2.42
See application file for complete search history.

(56) References Cited

U.S. PATENT DOCUMENTS

| | | | |
|---|---|---|---|
| 3,714,671 A | | 2/1973 | Edwards et al. |
| 3,755,823 A | * | 9/1973 | Hancock ...................... 623/2.18 |
| 4,172,295 A | * | 10/1979 | Batten ........................... 623/2.15 |
| 4,345,340 A | * | 8/1982 | Rosen ............................ 623/2.19 |
| 4,388,735 A | | 6/1983 | Ionescu et al. |
| 4,629,459 A | | 12/1986 | Ionescu et al. |
| 4,666,442 A | | 5/1987 | Arru et al. |
| 4,888,009 A | | 12/1989 | Lederman et al. |

(Continued)

FOREIGN PATENT DOCUMENTS

DE 100 50 092 A1 4/2002

(Continued)

OTHER PUBLICATIONS

"Mitroflow Aortic Pericardial Heart Valve; Instructions for Use", two pages, Sorin Group Canada Inc., Mitroflow Division, Burnaby, B.C., Canada, 2005.

(Continued)

*Primary Examiner* — David H Willse
*Assistant Examiner* — Tiffany Shipmon
(74) *Attorney, Agent, or Firm* — Lerner, David, Littenberg, Krumholz & Mentlik, LLP

(57) ABSTRACT

A prosthetic heart valve includes an annular stent having annularly spaced commissure portions. The tips of the commissure portions are preferably covered with fabric, and then additional fabric covers that fabric and the remainder of the stent, both inside and out (possibly also including a sewing ring insert at or near the base or inflow edge). The fabric is then covered by a layer of tissue, again both inside and out. A single sheet of additional tissue is mounted around the outside of the previously assembled components. This additional tissue forms the leaflet portions of the valve. The leaflet portions of the additional tissue are shaped by contact with a shaped mandrel, and the tissue of the structure is subjected to fixation (e.g., cross-linking) to produce a completed valve.

16 Claims, 8 Drawing Sheets

U.S. PATENT DOCUMENTS

| | | | |
|---|---|---|---|
| 5,037,434 A * | 8/1991 | Lane | 623/2.18 |
| 5,489,297 A | 2/1996 | Duran | |
| 5,549,665 A | 8/1996 | Vesely et al. | |
| 6,585,766 B1 * | 7/2003 | Huynh et al. | 623/2.38 |
| 6,610,088 B1 * | 8/2003 | Gabbay | 623/2.38 |
| 6,613,086 B1 * | 9/2003 | Moe et al. | 623/2.12 |
| 2001/0003007 A1 * | 6/2001 | Chinn et al. | 427/2.24 |
| 2002/0052651 A1 | 5/2002 | Myers et al. | |
| 2003/0171805 A1 * | 9/2003 | Berg et al. | 623/2.14 |
| 2004/0015233 A1 | 1/2004 | Jansen | |

FOREIGN PATENT DOCUMENTS

| | | |
|---|---|---|
| WO | WO 2004/012632 A | 2/2004 |
| WO | WO 2004/026173 A | 4/2004 |

OTHER PUBLICATIONS

"Mitroflow Aortic Pericardial Heart Valve"; five pages from Internet dated Jan. 26, 2007, Sorin Group Canada Inc., Mitroflow Division, 2006.

* cited by examiner

PROSTHETIC HEART VALVE INCLUDING STENT STRUCTURE AND TISSUE LEAFLETS, AND RELATED METHODS

This application claims the benefit of provisional application 60/875,921, filed Dec. 19, 2006, which is hereby incorporated by reference herein in its entirety.

BACKGROUND OF THE INVENTION

This invention relates to prosthetic heart valves, and more particularly to the type of prosthetic heart valves that use tissue material for the leaflets of the valve. The invention also relates to methods of making such valves.

There is increasing interest in artificial, prosthetic heart valves that use tissue material for the leaflets of the valve. Such valves tend to be less thrombogenic than mechanical prosthetic heart valves. This can reduce or eliminate the need for a patient who has received such a prosthesis to take anticoagulant medication on a long-term basis. Tissue-based heart valves may also have other advantages, such as quieter operation. Because of the interest in such valves, improvements to them are greatly desired. Improved methods of making such valves are also sought.

SUMMARY OF THE INVENTION

In accordance with certain aspects of the invention, a prosthetic heart valve includes an annular stent having a plurality of annularly spaced commissure portions, each of which has a tip. A fabric cover may be provided over each tip. An additional fabric covering may be provided over the fabric tip covers and the remainder of the stent. Tissue may be provided over the fabric covering. Additional tissue is provided around the outside of the previously mentioned components. This additional tissue includes leaflet portions that extend inwardly between annularly adjacent ones of the commissure portions.

In accordance with certain other aspects of the invention, a method of making a prosthetic heart valve includes providing an annular stent having a plurality of annularly spaced commissure portions, each of which has a tip. The method may further include covering each of the tips with a fabric tip cover. The method may still further include covering the tip covers and the remainder of the stent with an additional fabric cover. The method may further include covering the fabric cover with a tissue cover. The method may still further include wrapping additional tissue around the radially outer surface of the tissue cover, the additional tissue including leaflet portions that extend inwardly between annularly adjacent ones of the commissure portions.

Further features of the invention, its nature and various advantages, will be more apparent from the accompanying drawings and the following detailed description.

DETAILED DESCRIPTION

Figure 1:
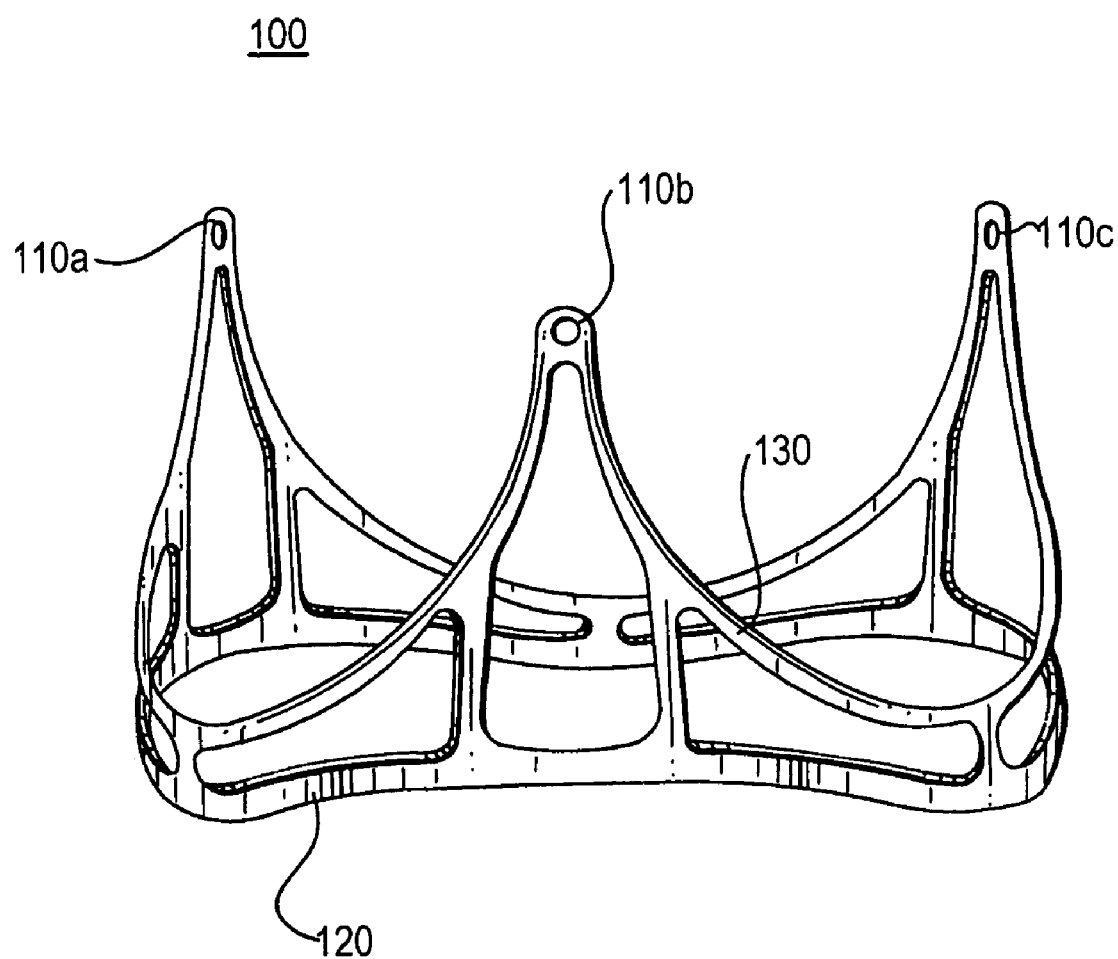
FIG. 1 is a simplified perspective view of a component of an illustrative embodiment of a prosthetic heart valve in accordance with the invention.

An illustrative embodiment of a first component 100 of an artificial heart valve in accordance with the invention is shown in FIG. 1. Component 100 is a hollow, annular, stent-like structure (sometimes referred to for convenience herein simply as a stent). Stent 100 is referred to as "hollow" because the interior that is bounded by its annular structure is open. Stent 100 is typically made of metal such as titanium (e.g., Ti 6Al-4V ELI Grade 5). A typical technique for making stent 100 is to cut it from a tube using a laser. Stent 100 is then typically electro-polished.

Because the valve of the illustrative embodiment being discussed is a tricuspid valve (e.g., for use in replacing a patient's aortic valve), stent 100 has three commissure portions or regions 110a, 110b, and 110c that are equally spaced from one another around the circumference of the stent. Each commissure portion stands up from the annularly continuous base portion of the stent. The base portion includes a lower-most, blood-inflow edge portion 120. This blood-inflow edge portion is scalloped as one proceeds around the stent to approximately match the natural scallop of the native valve annulus. In particular, this scallop rises in the vicinity of each commissure region, and it falls between each annularly adjacent pair of commissures.

Stent 100 also includes an annularly continuous blood-outflow edge portion 130 (which merges with and becomes part of each commissure region 110 at the commissures). Outflow edge portion 130 is much more deeply scalloped than the inflow edge portion. In particular, outflow edge portion 130 rises adjacent each commissure 110 (actually merging into each commissure as noted above), and falls between each annularly adjacent pair of commissures.

The inflow edge 120, outflow edge 130, and flexibility of stent 100 are designed to help ensure proper opening and coaptation of the finished valve in use. (Coaptation is the coming together of the outflow portions of the valve leaflets when the valve is closed.) Stent 120 is further designed to decrease maximum stresses in the stent in use, which gives the finished valve an increased safety factor.

Although titanium is mentioned above as a typical material from which stent 100 can be made, other materials are also possible. Some examples of other materials that may be suitable for use in making stent 100 include Elgiloy MP35N or polymers such as PEEK or acetal.

Figure 2:
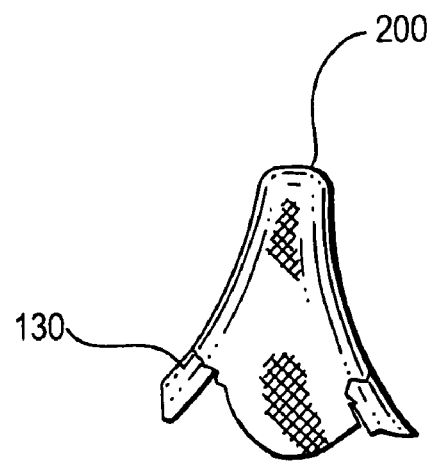
FIG. 2 is a simplified perspective view of a representative portion of FIG. 1 with another representative component added in accordance with the invention.

FIG. 2 illustrates a subsequent possible step in the manufacture of the illustrative embodiment being described. This is the addition of a sleeve-like fabric covering 200 over the top of each commissure post. Fabric commissure tip covers 200 help reduce the possibility that the stent commissure tips may poke through subsequently added components. An illustrative fabric that is suitable for use in making coverings 200 is reemay fabric, which is a spun form of polyester. Each tip cover 200 may be secured to the associated commissure tip with sutures.

Figure 3:
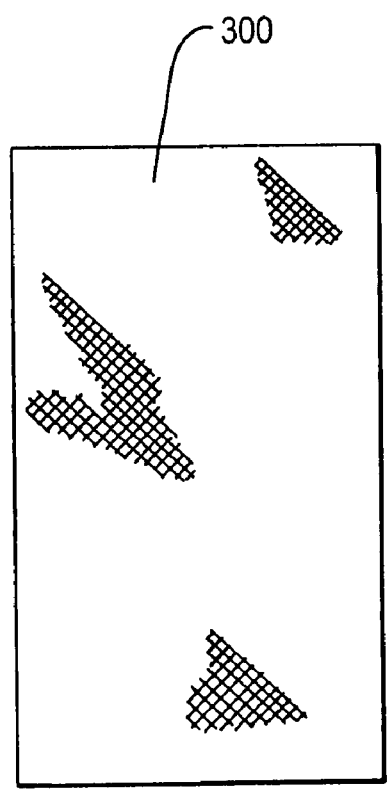
FIG. 3 is a simplified elevational view of another component prior to assembly with other components in accordance with the invention.
Figure 4:
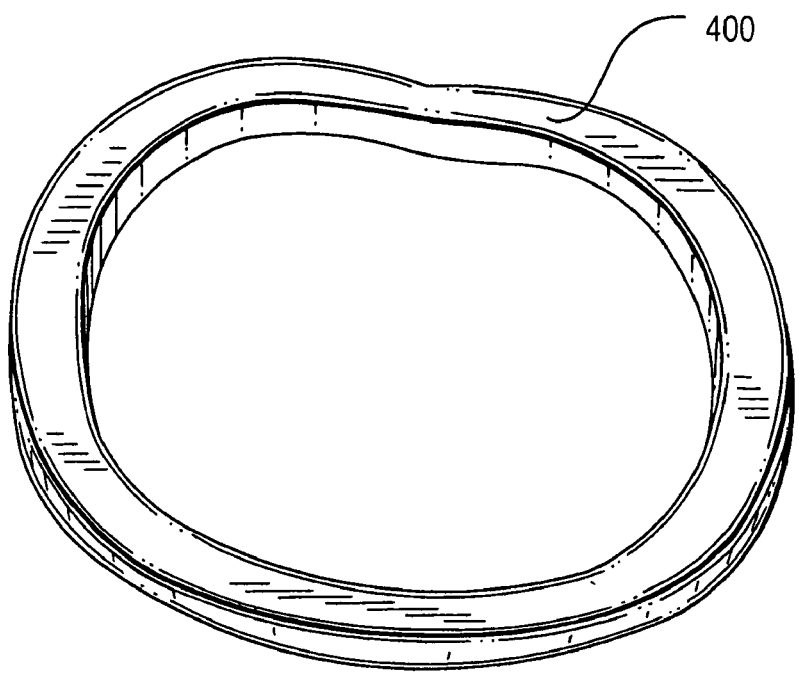
FIG. 4 is a simplified elevational view of yet another component prior to assembly with other components in accordance with the invention.
Figure 5:
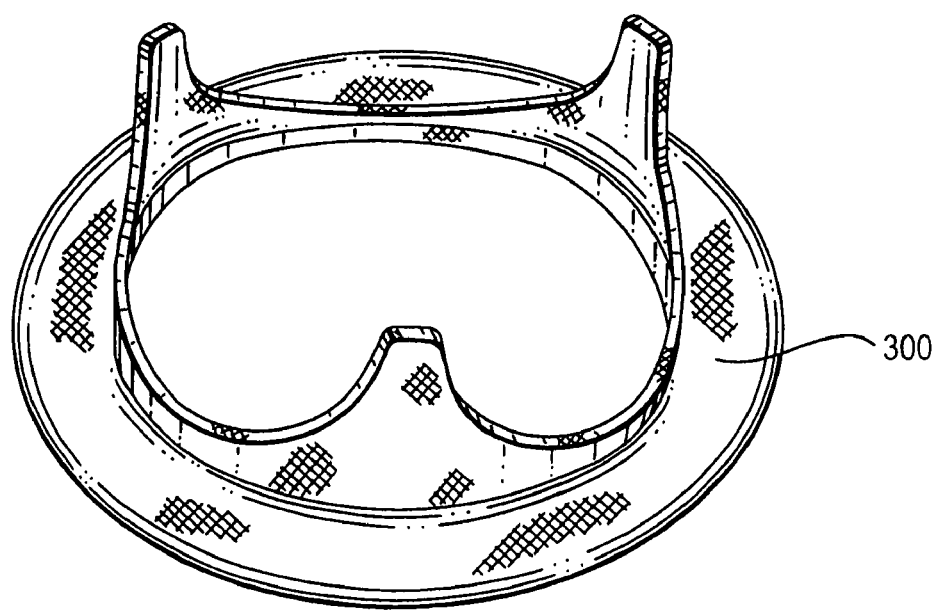
FIG. 5 is a simplified perspective view of an assembly of the components from FIGS. 1-4 in accordance with the invention.

FIGS. 3-5 illustrate further possible components and steps in the manufacture of the illustrative embodiment being described. FIG. 3 shows an illustrative embodiment of a polyester fabric tube 300; FIG. 4 shows an illustrative embodiment of a silicone cuff filler ring 400; and FIG. 5 shows an assembly 500 that includes stent 100 (with post tip coverings 200) and silicone cuff filler ring 400 covered inside and out by fabric tube 300. For example, stent 100 (with coverings 200) and ring 400 may be placed coaxially around the outside of a lower portion of fabric tube 300. Ring 400 may be located outside inflow edge portion 120. The upper portion of sleeve 300 may then be pulled down over the outside of components 100 and 400 and pulled tightly enough to conform to outflow edge portion 130 as shown in FIG. 5. Sutures may be used to hold the above-described components together in the condition shown in FIG. 5. In particular, all of components 100, 200, and 400 are completely covered inside and out by fabric 300. Ring 400 is located adjacent inflow edge portion 120 and follows the scalloping of inflow edge portion 120 all the way around assembly 500. The upper portion of fabric 300 conforms closely to stent 100 above ring 400, and in particular, the upper portion of the fabric follows the scalloped outflow edge portion 130 all the way around assembly 500.

Figure 6:
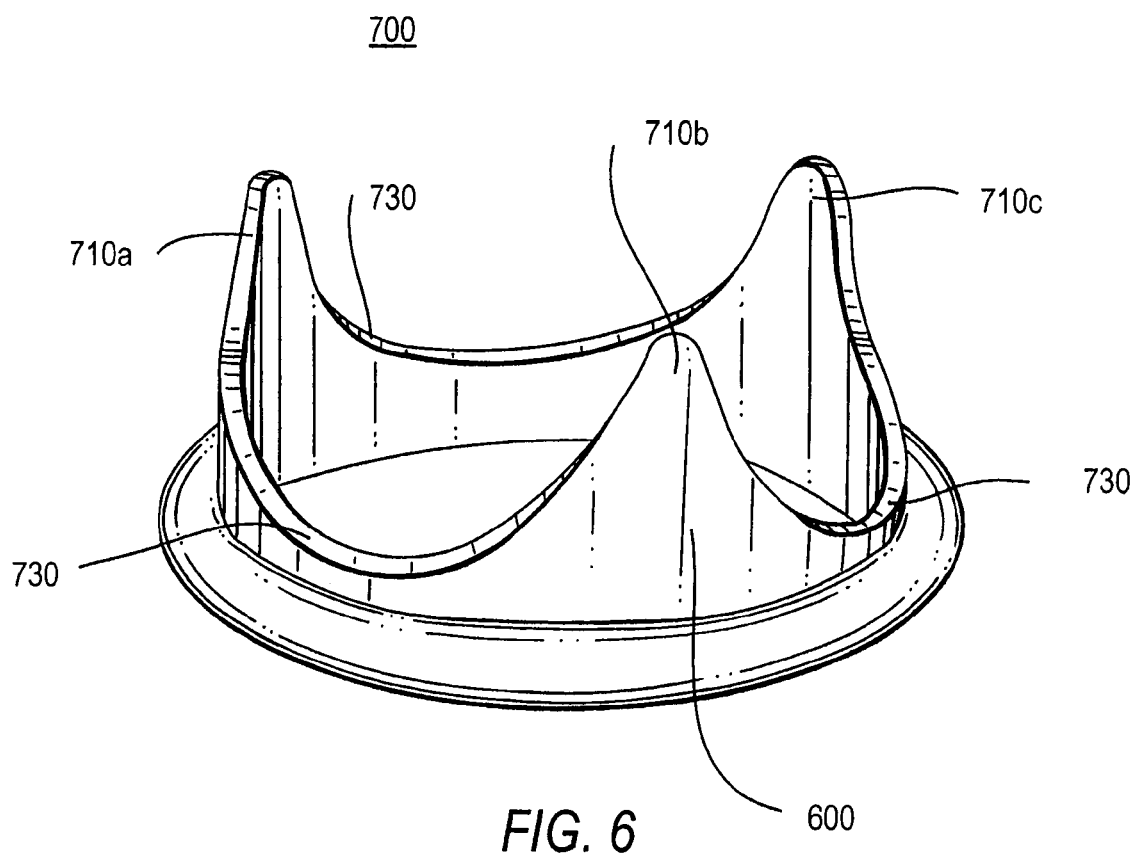
FIGS. 6 and 7 are respectively simplified perspective top and bottom views of the FIG. 5 assembly with another component added in accordance with the invention.
Figure 7:
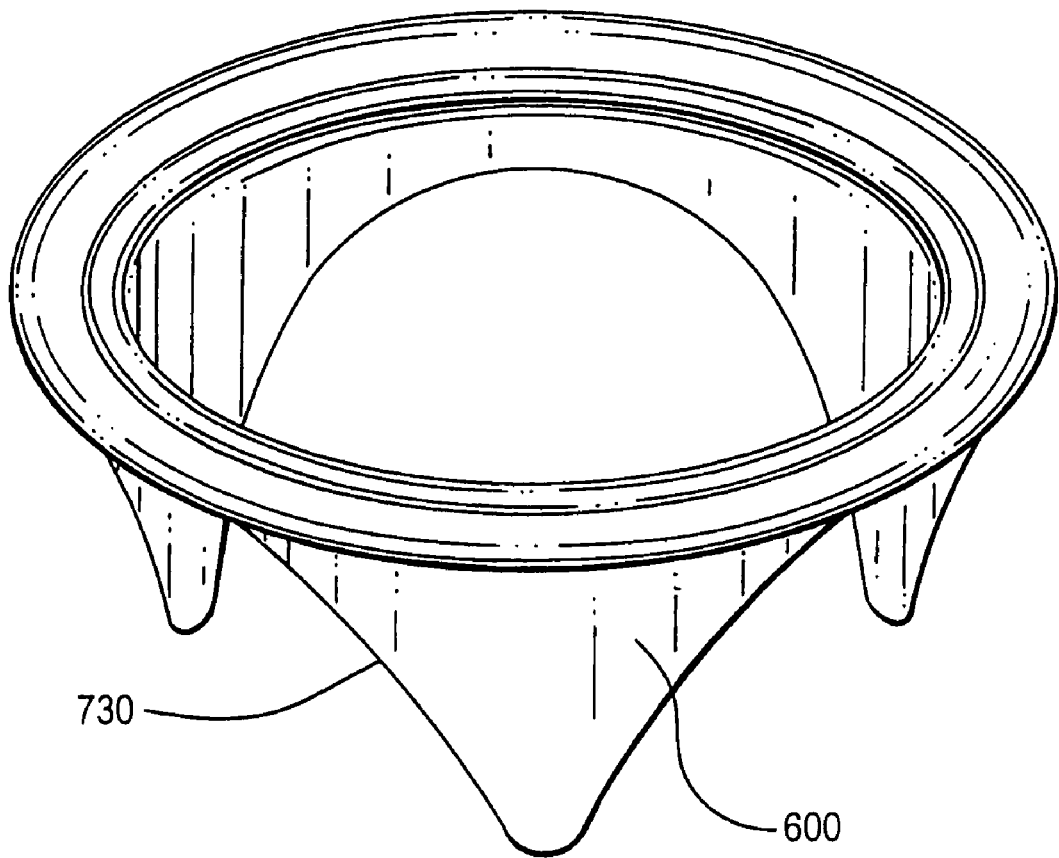

FIGS. 6 and 7 illustrate still further possible components and steps in the manufacture of the illustrative embodiment being described. In particular, these FIGS. illustrate the addition of porcine pericardium tissue 600 over assembly 500, both inside and out, to produce assembly 700. One of the purposes of this is to enhance durability of the finished valve. Another purpose is to reduce thrombogenicity of the finished valve. Sutures may be used to secure tissue 600 to assembly 500 as shown in FIGS. 6 and 7. Apart from somewhat thickening assembly 700 as compared to assembly 500, the addition of tissue 600 does not significantly change the shape of any portion of the structure.

Although porcine pericardium is mentioned above for component 600, other types of tissue may be used instead if desired. Examples of such other possible tissue for component 600 include any mammalian pericardium (e.g., equine or bovine pericardium).

Figure 8:
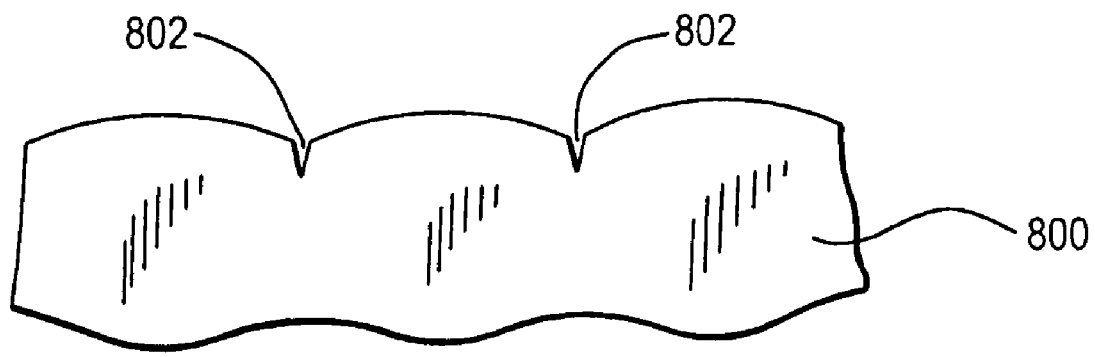
FIG. 8 is a simplified perspective view of another component prior to assembly with the other components in accordance with the invention.

FIG. 8 illustrates a further possible component and steps in the manufacture of the illustrative embodiment being described. As shown in FIG. 8, component 800 is a sheet of bovine pericardium that has been die cut to a shape that can be used to form all three leaflets of a finished valve. Note that the lower edge of sheet 800 (as viewed in FIG. 8) is scalloped to conform to the blood-inflow edge (like 120 in FIG. 1) of the finished valve. The upper portion of sheet 800 (as viewed in FIG. 8) will form the three leaflets of the valve. There are shallow downward cuts 802 between the individual leaflet portions adjacent the upper edge of sheet 800, but sheet 800 remains intact so that this single sheet of tissue can be used to form all three leaflets in the finished valve.

Although bovine pericardium is mentioned above for component 800, other types of tissue may be used instead if desired. Examples of such other possible tissue for component 800 include any mammalian pericardium (e.g., equine or porcine pericardium).

Figure 9:
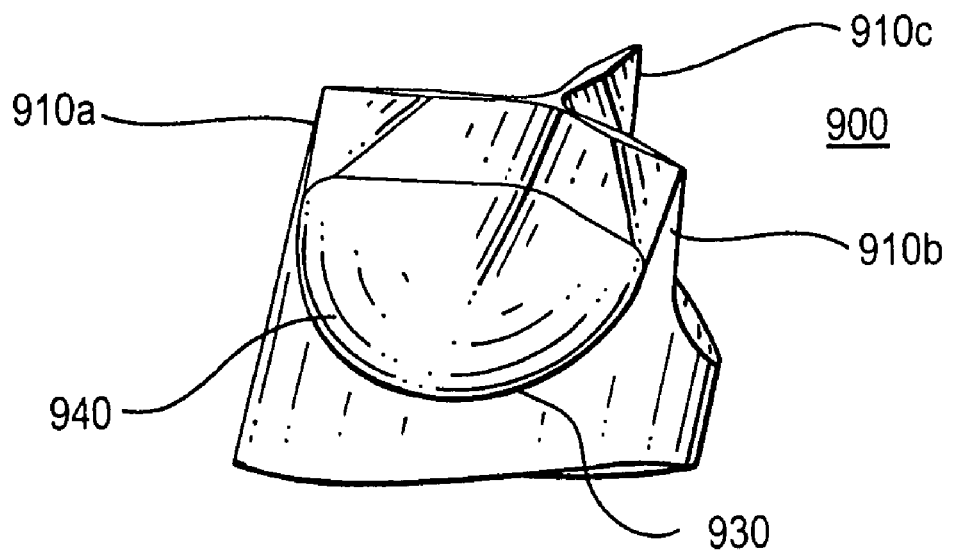
FIG. 9 is a simplified perspective view of a tool that is useful at a certain stage in the manufacture of heart valves in accordance with the invention.

FIG. 9 illustrates a tool 900 that can be used in further steps in manufacturing the illustrative embodiment being described. Tool 900 is a mounting mandrel which can be inserted coaxially into assembly 700. In particular, this is done so that each of the commissure portions 910a-c of mandrel 900 is angularly or rotationally aligned with a respective one of the commissure portions 710 of assembly 700. In addition, each of the scalloped edge portions 930 of mandrel 900 is adjacent a corresponding scalloped outflow edge portion 730 of assembly 700.

Figure 10:
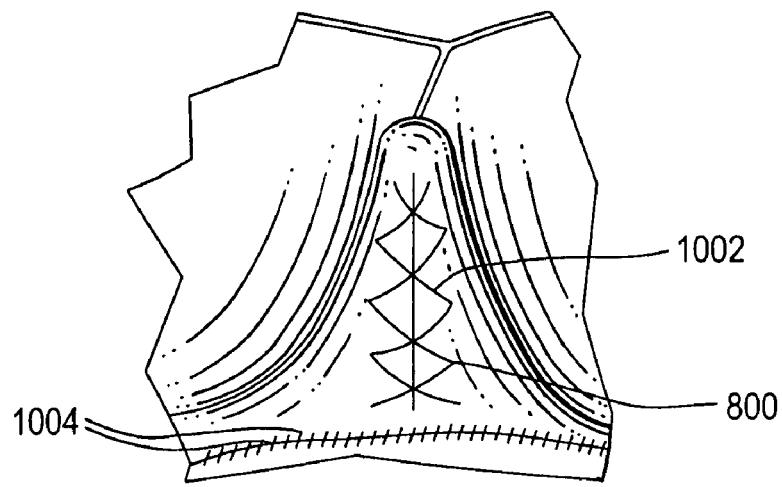
FIG. 10 is a simplified elevational view of a representative portion of an assembly of components in accordance with the invention.

With mandrel 900 positioned inside assembly 700 as described in the preceding paragraph, tissue 800 is wrapped around the outside of assembly 700 above the sewing cuff portion of assembly 700. The sewing cuff portion is the portion that includes ring 400 in its interior. This wrapping is done with the scalloped lower edge (FIG. 8) of tissue 800 just above and conformed to the scalloped sewing cuff of assembly 700. In addition, each of cuts 802 is adjacent a respective one of two of commissures 710, and the extreme left and right edges of tissue 800 come together adjacent the third one of commissures 710. The portion of tissue 800 above each of outflow edge scallops 730/930 is pressed radially inwardly so that it resets on the adjacent concave surface 940 of mandrel 900. Tissue 800 is stitched to assembly 700 (but not to mandrel 900) in this condition. For example, FIG. 10 shows stitching 1002 that is used to hold the initially free, left and right edges of tissue 800 together adjacent one of the commissures 710 of assembly 700. Other stitching 1004 in FIG. 10 is used to stitch tissue 800 to assembly 700 annularly all the way around assembly 700 just above the sewing ring portion of assembly 700. The valve structure shown in FIG. 10 may be referred to as assembly 1000.

Figure 11:
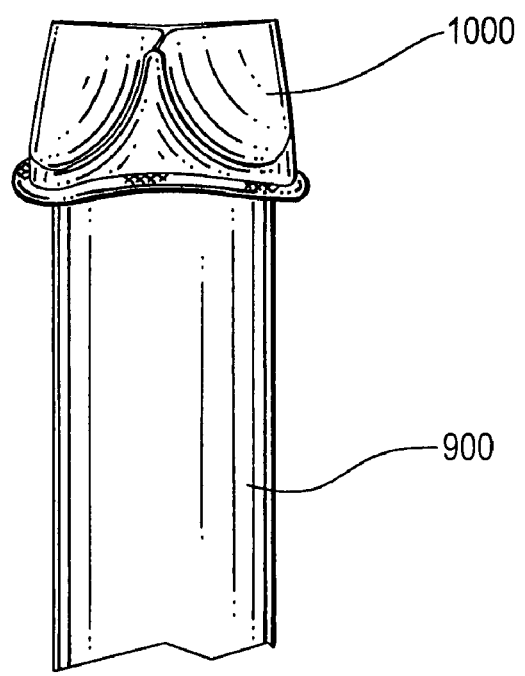
FIG. 11 is a simplified perspective view of an assembly in accordance with the invention on a tool like that shown in FIG. 9.

FIG. 11 illustrates a possible further step in manufacturing the illustrative embodiment being described. FIG. 11 shows an assembly 1000 still on a mandrel 900 as described in the immediately preceding paragraphs. Note in particular that the portion of tissue 800 above each of outflow edge scallops 730 remains pressed in against the adjacent concave surface 940 of mandrel 900. With assembly 1000 in this condition on mandrel 900, assembly is subject to fixation of the tissue. Such fixation of the tissue may be by any conventional and suitable means and may include cross-linking of the tissue by exposing it to cross-linking agents such as glutaraldehyde or epoxides such as TGA (triglycidyl amine). Such fixation of the tissue stabilizes the tissue and renders it substantially biologically inert and bio-compatible. Such fixation of the tissue in contact with shaped surfaces 940 also gives the tissue a bias to return to that shape when it is not subjected to external forces. On the other hand, the fixation still leaves the tissue sufficiently flexible that the leaflet portions of tissue 800 above outflow edge scallops 730 can deflect outwardly to open the valve and let blood flow out when a ventricular contraction pressurizes the blood in the ventricle below the valve. When that ventricular pressure ceases, however, the leaflet portions above outflow edge scallops 730 come together again (coapt) and close the valve.

Figure 12:
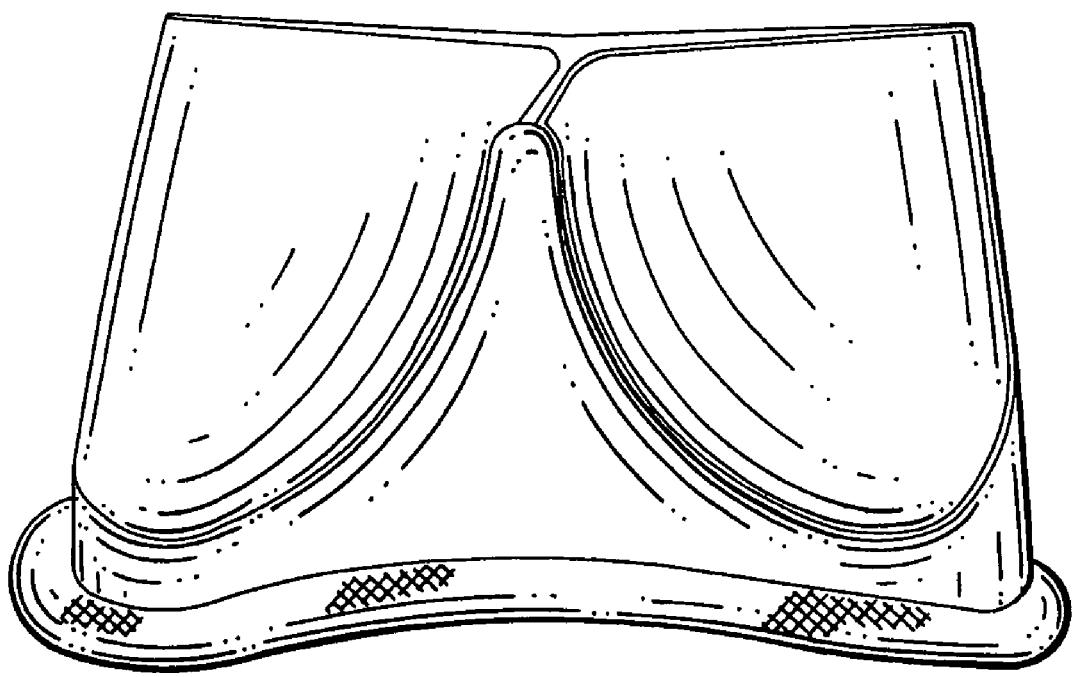
FIG. 12 is a simplified perspective of an illustrative embodiment of a completed prosthetic heart valve in accordance with the invention.

After the tissue of assembly 1000 has been subjected to fixation as described above, assembly 1000 can be removed from mandrel 900. The result is a finished valve 1200 as shown in FIG. 12. In use, valve 1200 has the operating characteristics described in the preceding paragraphs.

It will be understood that the foregoing is only illustrative of the principles of the invention, and that various modifications can be made by those skilled in the art without departing from the scope and spirit of the invention. For example, the shapes and/or sizes of various components can be different from the shapes and sizes shown herein. As another example, the materials used for various components can be different from those mentioned specifically herein.

What is claimed is:

1. A prosthetic heart valve comprising:
    an annular stent having annularly spaced commissure portions, each commissure portion including a tip;
    a first fabric cover over each tip, the first fabric cover not extending to the remainder of the annular stent;
    a second fabric cover that extends over the first fabric cover and the remainder of the annular stent;
    a first tissue membrane covering the first fabric cover and the second fabric cover; and
    a second tissue membrane which surrounds the outside of the first tissue membrane, the first fabric cover and the second fabric cover; wherein the second tissue membrane forms leaflet portions that extend inwardly between the commissure portions.

2. The prosthetic heart valve defined in claim 1 wherein the stent is made of metal.

3. The prosthetic heart valve defined in claim 1 wherein the first fabric cover comprises reemay fabric.

4. The prosthetic heart valve defined in claim 1 wherein the second fabric cover comprises polyester fabric.

5. The prosthetic heart valve defined in claim 1 wherein the first tissue membrane comprises porcine pericardium tissue.

6. The prosthetic heart valve defined in claim 1 wherein the second tissue membrane comprises bovine pericardium tissue.

7. The prosthetic heart valve defined in claim 1 further comprising:
    a sewing cuff structure adjacent an edge of the valve that is axially opposite the commissure tips.

8. The prosthetic heart valve defined in claim 7 wherein the sewing cuff comprises a ring of filler material.

9. The prosthetic heart valve in claim 8 wherein the ring of filler material is disposed inside the second fabric cover.

10. The prosthetic heart valve defined in claim 9 wherein the ring of filler material comprises silicone.

11. The prosthetic heart valve defined in claim 1 wherein the second tissue membrane has been subjected to fixation after being assembled around the outside of the first tissue membrane, the first fabric cover and the second fabric cover.

12. The prosthetic heart valve defined in claim 11 wherein the second tissue membrane has been subjected to the fixation while the leaflet portions are shaped to extend inwardly between the commissure portions.

13. The prosthetic heart valve defined in claim 12 wherein the second tissue membrane has been subjected to the fixation while the leaflet portions are shaped, in contact with a shaping surface, to extend inwardly between the commissure portions.

14. The prosthetic heart valve of claim 1, wherein each commissure portion includes a first edge and a second edge, the first and second edges defining a space therebetween, the first fabric cover covering the space defined between the first and second edges.

15. A prosthetic heart valve comprising: an annular stent having annularly spaced commissure portions, each commissure portion having a tip and a remaining commissure portion, each tip having an inside surface and an outside surface; a first fabric cover substantially covering the inside and outside surfaces of each tip, but not covering each remaining commissure portion; a second fabric cover that extends over the first fabric cover and the remainder of the annular stent; a first tissue membrane covering the inside and outside of the first fabric cover and the second fabric cover; and a second tissue membrane which surrounds the outside of the first tissue membrane, the first fabric cover and the second fabric cover; wherein the second tissue membrane forms leaflet portions that extend inwardly between the commissure portions.

16. The prosthetic heart valve of claim 15, wherein each commissure portion includes a first edge and a second edge, the first and second edges defining a space therebetween, the first fabric cover covering the space defined between the first and second edges.

* * * * *